United States Patent [19]

Christiansen

[11] 4,058,447
[45] Nov. 15, 1977

[54] ELECTROCHEMICAL MEASURING ELECTRODE

[75] Inventor: Torben Falch Christiansen, Holte, Denmark

[73] Assignee: Radiometer A/S, Copenhagen, Denmark

[21] Appl. No.: 656,873

[22] Filed: Feb. 10, 1976

[30] Foreign Application Priority Data

Feb. 13, 1975   Denmark ............................. 532/75

[51] Int. Cl.$^2$ ............................................. G01N 27/46
[52] U.S. Cl. ................................................. 204/195 P
[58] Field of Search ............... 204/1 P, 195 P; 324/29

[56] References Cited

U.S. PATENT DOCUMENTS

| | | | |
|---|---|---|---|
| 3,505,195 | 4/1970 | Nielsen et al. | 204/195 P |
| 3,515,658 | 6/1970 | Amdur | 204/195 P |
| 3,803,006 | 4/1974 | Krueger et al. | 204/1 F |
| 3,830,709 | 8/1974 | Krueger et al. | 204/1 N |
| 3,839,178 | 10/1974 | Macur | 204/195 P |
| 3,896,020 | 7/1975 | Le Blanc | 204/195 M |
| 3,957,613 | 5/1976 | Macur | 204/195 M |

FOREIGN PATENT DOCUMENTS 1,917,179   10/1970   Germany ........................... 204/195 P

*Primary Examiner*—G. L. Kaplan
*Attorney, Agent, or Firm*—Hubbell, Cohen, Stiefel & Gross

[57] ABSTRACT

An electrode for polarographic measurement of the partial pressure of oxygen in gases or solutions, comprising a cathode in contact with and outwardly shielded by a gas permeable membrane, a silver/silver bromide half cell serving as anode, and a bromide-containing aqueous electrolyte in contact with the anode and the cathode, the bromide ion concentration of the electrolyte being between $10^{-4}$ and $5 \times 10^{-3}$M, preferably $5 - 6 \times 10^{-4}$M.

2 Claims, 3 Drawing Figures

ELECTROCHEMICAL MEASURING ELECTRODE

BACKGROUND OF THE INVENTION

The present invention relates to an electrode for polarographic measurement of the partial pressure of oxygen in gases or solutions.

Electrodes of this kind, also called "Clark electrodes," are known and used in various technical fields, inter alia for determining the partial pressure of oxygen in blood, but also for determining the partial pressure of oxygen in other liquids and in gases.

These electrodes comprise a cathode in contact with and outwardly (in other words, in the direction of the medium to be measured) shielded by a gas permeable membrane, a half cell serving as an anode, this being a silver/silver halide half cell, usually simply a silver strip covered with silver halide, and a halogen-containing aqueous electrolyte which is in contact with the cathode and the anode. In the electrodes of this type used in practice, the halide is chloride.

When using such an electrode for polarographic oxygen determination, a constant potential is applied between the anode and the cathode. Oxygen from the solution or the gas to be measured diffuses through the membrane and is reduced to hydrogen peroxide and/or water on the cathode, which results in an electrical current, the magnitude of which is dependent upon the $O_2$-concentration in the measured medium. By means of suitable current measuring equipment of known type, this electrical current is measured, and the oxygen partial pressure in the measured medium is calculated on the basis of the current measurement; in practice, the current measuring equipment is usually so calibrated that the calculted oxygen pressure corresponding to the current can be directly read in mm Hg.

In the known art electrodes of this type in which the anode is an Ag/AgCl half cell and the electrolyte usually contains NaCl in a concentration of about 0.13M, the optimum polarisation voltage will be $-630$ mV, in other words, the voltage of the cathode is $-630$ mV, in relation to the voltage of the anode, as it has been found that the best linear relation between $O_2$ concentration in the measured medium and the polarisation current is obtained at this polarisation voltage. At higher or lower polarisation voltages, the current will vary in a more or less non-linear manner. Therefore, for the major part, existing apparatus for $O_2$ measurement using oxygen electrodes of the type here described, for example, for use in connection with micro-sized oxygen electrodes for measuring the partial pressure of oxygen in blood, is adapted to work with a polarisation voltage of $-630$ mV.

In electrodes of the type mentioned, the magnitude of the electrical current measured is also dependent upon the area of the cathode. Unfortunately, the cathode area in the existing electrodes has been found to increase continuously during the use of the electrode, which is due to the fact that silver from the half cell serving as the anode is being dissolved in the electrolyte and from there reduced out as free silver on the cathode. Naturally, this incurs an undesirable drift of the electrode response on given partial pressures of $O_2$ in the measured medium and, therefore, constitutes a considerable source of measurement inaccuracy, especially when the cathode is small, for example, smaller than about 100 $\mu$, such as is often the case in modern electrodes for the measurement of the partial pressure of oxygen in blood.

SUMMARY OF THE INVENTION

The present invention aims at solving the above-mentioned problem involving drift caused by increasing cathode area and provides electrodes of the kind stated above wherein the anode is a silver/silver bromide half cell, and the electrolyte contains bromide ion in a concentration between $10^{-4}$M and $5 \times 10^{-3}$M.

It has been found that the silver deposit on the cathode and, consequently the drift of the electrode, will be minimized when the anode is a silver/silver bromide half cell and the electrolyte contains bromide in a concentration within the above-mentioned limits.

Furthermore, it has been found that the electrode according to the present invention with a silver/silver bromide half cell and a bromide concentration in the electrolyte solution within the above-stated interval may be used in combination with already existing apparatus adapted to work at a polarisation voltage of $-630$ mV. More specifically, the optimum polarisation voltage in an electrode according to the invention will be $-630$ mV when the bromide concentration in the electrolyte is $5 - 6 \times 10^{-4}$M.

DETAILED DESCRIPTION

Figure 1:
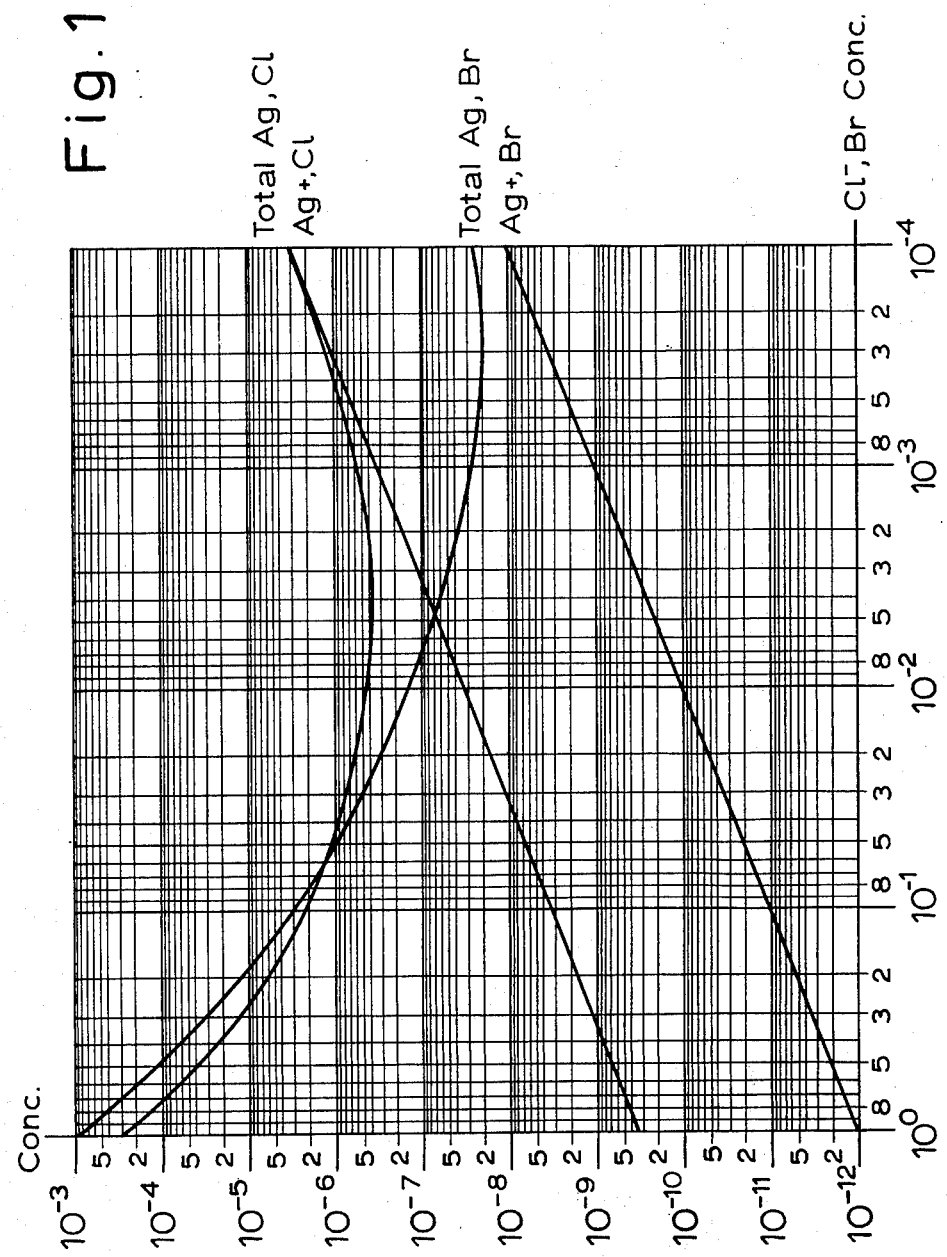
Figure 2:
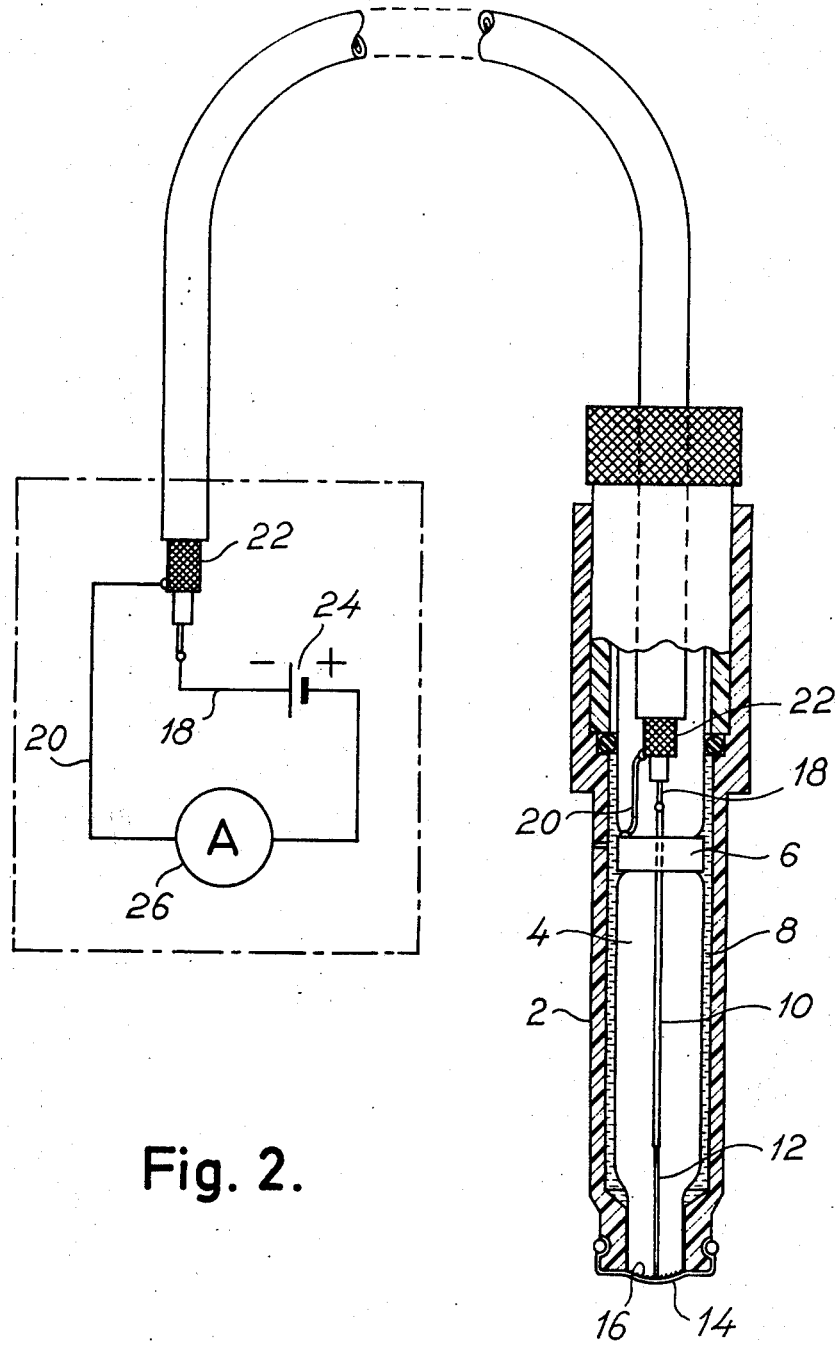
Figure 3:
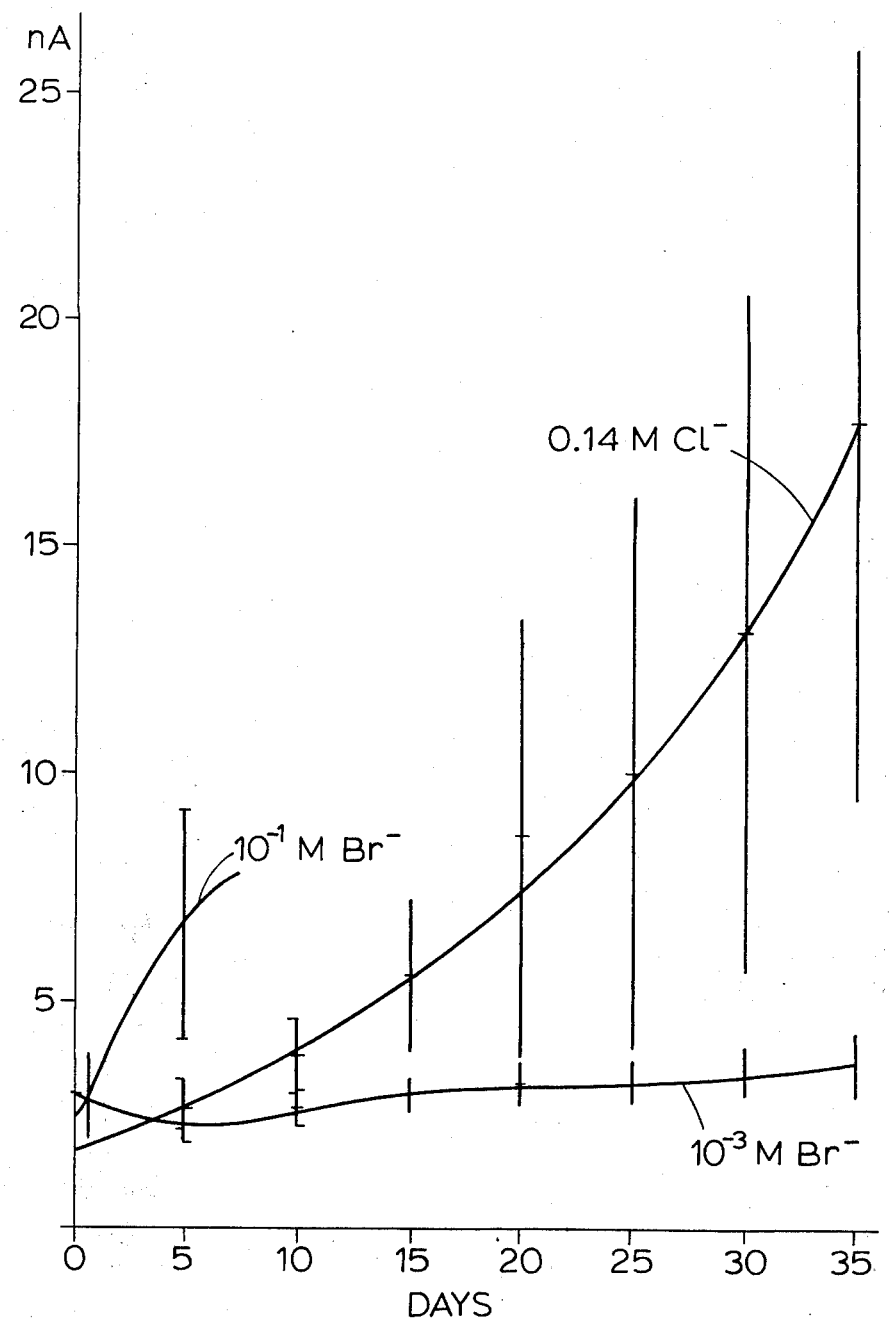

The invention will now be described in further detail with a reference to the drawing in which:

FIG. 1 is a graph showing the total concentration of silver in the electrolyte as a function of the halide ion concentration, FIG. 2 shows an embodiment of an electrode according to the invention, and FIG. 3 is a graph showing the measured current as a function of time for electrodes according to the invention and electrodes of known type, respectively.

In FIG. 1, the lowest curve shows the concentration of $Ag^+$ as a function of the $Br^-$ concentration in an electrolyte containing, as halide ion, the bromide ion and being in equilibrium with an Ag/AgBr half cell. For the same system, the total content of dissolved Ag in the electrolyte, that is Ag dissolved as $Ag^+$ and Ag dissolved in various complex forms (AgBr, $AgBr_2^-$, $AgBr_3^{--}$, $AgBr_4^{---}$) is shown (the curve is designated "Total Ag, Br"). Corresponding to this set of curves, FIG. 1 shows the analogous curves for the $Ag^+$ content in an electrolyte in which the halide ion content is the chloride ion, and which is in equilibrium with an Ag/AgCl half cell, as well as for the total content of dissolved silver in the said electrolyte. Also in the latter case, the curve representing the $Ag^+$ content is a straight line.

It is evident from FIG. 1 that at bromide ion concentrations in the range used according to the invention, that is between $10^{-4}$ and $5 \times 10^{-3}$, the total amount of dissolved silver is below $10^{-7}$ and descends to as low as $2 \times 10^{-8}$M. For comparison, in the commonly used electrode in which the electrolyte contains NaCl in a concentration of 0.13M, the total concentration of dissolved silver will be about $3 \times 10^{-6}$, such as appears from FIG. 1, in other words, about a hundred times as large as in the electrode according to the invention. As the extent of silver deposit on the cathode in an electrode of the type described here depends on the total amount of dissolved silver, it is evident that the silver deposit in an electrode according to the invention is minimized in comparison with the known art electrode.

FIG. 1 also shows another interesting fact, that is, that with obtainment of the above-mentioned advantages of the invention with respect to minimizing the silver deposit on the cathode, it is possible to construct an electrode according to the invention in such a manner that it may be used in connection with the existing apparatus adapted to a polarisation voltage of −630 mV.

The optimum applied polarisation voltage depends on the concentration of $Ag^+$, and in the known art electrodes, in which the chloride ion concentration is about 0.13M, the $Ag^+$ concentration is about $2 \times 10^{-9}$, as will appear from FIG. 1. Considering an Ag/Br half cell in equilibrium with a bromide ion-containing electrolyte (the bottom curve of FIG. 1), it will be seen that a corresponding $Ag^+$ concentration is present for a bromide ion concentration in the electrolyte of $5 - 6 \times 10^{-4}$, in other words, a value within the range of the invention and very close to the minimum for the total silver content in the electrolyte. Hence, it will be seen that by choosing the bromide ion concentration of $5 - 6 \times 10^{-4}$ in the electrolyte, one is enabled, on the one hand to have a miminum of silver deposit on the cathode, and on the other hand, to have an electrode which is immediately suited for working together with the existing apparatus.

Admittedly, it has previously (cfr. German Offenlegungsschrift No. 1,917,179, publication date Oct. 8, 1970) been proposed to make an electrode for polarographic oxygen determination with an electrolyte consisting of salts which, with silver ions, form a more heavily soluble compound than AgCl, e.g. KBr, and the purpose of this was just to prevent the precipitation of metallic silver at the cathode; however, the said German Offenlegungsschrift does not at all deal with the question of the total concentration of dissolved silver which is in fact decisive to the silver precipitation and, hence, does not lead to the critical range of concentration which in fact is decisive to the obtainment of the desired effect. The sole numerical statement of bromide concentration in the Offenlegungsschrift appears from claim 3 thereof, according to which an electrolyte with a potassium bromide concentration of 2% is used, which corresponds to a bromide ion concentration of about 0.16M. As will be seen from FIG. 1, the total amount of dissolved silver at this bromide ion concentration is $10^{-5}$, which concentration is higher than both for the conventional Ag/AgCl−0.13M NaCl electrode used in practice and (even) for an electrode with 0.16M chloride ion concentration. Hence, the German Offenlegungsschrift does not in any way anticipate the present invention, as the combination of Ag/AgBr and bromide ion-containing electrolyte described in the Offenlengungsschrift will give rise to even greater silver deposit on the cathode than with the Ag/AgCl anode with chloride ion-containing electrolyte commonly used in the art, whereas, with the electrode according to the present invention, there is obtained a more than a hundred-fold reduction of the total silver concentration present in the electrolyte, which total concentration is decisive to the silver deposit.

U.S. Pat. No. 3,515,658 relates to an electrochemical cell for measuring gases wherein the cell electrolyte essentially contains sulfide ions and the anode comprises silver, lead, copper, tin, mercury, or mercury amalgam. The sulfide ion does not form complex with silver, and hence, in the cell disclosed in the said U.S. patent, the electrolyte will contain a very low concentration of dissolved silver. However, there are some problems involved in using sulfide ion in an oxygen electrode: sulfide is oxidized by oxygen, and oxygen electrodes used in biological fluids will be exposed to carbon dioxide, which liberates hydrogen sulfide from the sulfide electrolyte. Also sulfide or hydrogen sulfide may poison the cathode, especially if the cathode is of platinum. In the electrode of the present invention, these problems do not occur.

FIG. 2 shows an embodiment of an electrode according to the invention. In a housing 2 of an inert material, e.g. a suitable plastic material such as "Delrin," is arranged a glass container 4, closed at the bottom end, and surrounded by a band-shaped Ag/AgCl half cell 6. The aqueous eletrolyte 8 is present in the space between the housing 2 and the glass container 4. A silver thread 10 extends through the glass container and, at its lower end, passes into a platinum thread 12 with a small diameter, typically less than 100 $\mu$, for example 20 $\mu$. At its lower end, the platinum thread is embedded in the glass container in such a manner that one end of the platinum thread is exposed and faces towards a gas permeable membrane 14 which is adapted to be brought into contact with the measured medium. At a contact point, the silver thread 10 passes into the interior conductor 18 of a cable 22, the other conductor 20 of which (in the present case, the cable is shown as an ordinary shield cable) is in contact with the Ag/AgCl half cell. The conductor 18 leads to the negative terminal, and the conductor 20 to the positive terminal of a voltage source 24, and a current measuring device 26 is included in the circuit.

The voltage source 24 and the current measuring device 26 usually form part of the conventional measuring apparatus to which the electrode is connected by means of conventional electrical plugs.

The Ag/AgBr half cell is usually suitably formed as a silver band covered with silver bromide, but also any other embodiment of an Ag/AgBr half cell may be used. The electrolyte 8 contains a readily soluble bromide, for example potassium bromide, sodium bromide or calcium bromide, in a bromide ion concentration in the range between $10^{-4}$ and $5 \times 10^{-3}$ according to the invention, and in a preferred embodiment adapted to existing apparatus, in a range of about $5 - 6 \times 10^{-4}$. In addition, the electrolyte will usually contain components which are conventional in electrodes of the type in question, for example, a phosphate buffer at the pH of blood (about 7.4) when the electrode is to be used for determining the partial pressure of oxygen in blood. Additional constituents may also be present in the electrolyte without detracting from the advantages obtained according to the invention. For example, even chloride ion may be present in smaller amounts, for example, up to the same order as the bromide ion concentration (and will often be present as impurity), without any substantial change of the beneficial effect of the use of bromide in the concentration range of the invention. The electrolyte is in contact with the cathode, that is, the exposed end of the platinum thread, for example, in that the lower surface of the glass container 4, which is in contact with the membrane 14, is ground in course grooves 16 which permit electrolyte to penetrate the grooves.

Evidently, an electrode according to the invention may be designed in various other suitable ways which will depend upon considerations concerning production and use, but it is a common feature to all electrodes of the present kind that they comprise a cathode of a noble or relatively noble metal such as platinum, gold or silver, an Ag/AgBr half cell and an electrolyte with a bromide ion concentration between $10^{-4}$ and $5 \times 10^{-3}$, which electrolyte is in contact with the half cell and with the cathode, and, relative to the measured medium, with the cathode (and the electrolyte and the anode) being arranged behind a gas permeable membrane. In the typical case, the voltage source 24 will be one which applies a voltage of $-630$ mV on the anode, relative to the cathode.

COMPARATIVE EXAMPLE

A comparative experiment was made using 12 electrodes of the construction shown in FIG. 2. In 4 of these electrodes, the electrolyte contained disodium hydrogen phosphate in a concentration of 0.3M, potassium hydrogen phosphate in a concentration of 0.2M and potassium chloride in a concentration of 0.14M; hence these 4 electrodes are conventional electrodes representing the state of the art. In 8 of the electrodes, the electrolyte contained disodium hydrogen phosphate in a concentration of 0.3M, potassium dihydrogen phosphate in a concentration of 0.2M and potassium bromide in a concentration of 0.001M; hence, these 8 electrodes according to the present invention.

The 12 electrodes were used under identical conditions for polarographic determination of the partial pressure of oxygen in water saturated with atmospheric air at 37° C. The table below sets out the mean values for the measured current in nA as a function of the time for the 4 conventional electrodes and the 8 electrodes according to the invention, respectively.

TABLE

| Days | Conventional electrode | Standard deviation | Electrode according to the invention | Standard deviation |
|---|---|---|---|---|
| 0 | 1.7 | ± 0.35 | 3.0 | ± 0.88 |
| 5 | 2.8 | ± 0.55 | 2.3 | ± 0.38 |
| 10 | 3.8 | ± 0.81 | 2.7 | ± 0.38 |
| 15 | 5.6 | ± 1.6 | 3.0 | ± 0.37 |
| 20 | 8.7 | ± 4.8 | 3.3 | ± 0.48 |
| 25 | 10.1 | ± 6.0 | 3.2 | ± 0.50 |
| 30 | 13.1 | ± 7.5 | 3.5 | ± 0.62 |
| 35 | 17.8 | ± 8.4 | 3.6 | ± 0.70 |

It appears from the values for the current that the conventional electrodes show a very large drift, whereas the electrodes according to the invention show minimum drift. The striking difference between conventional electrodes and the electrode according to the invention appears from FIG. 3, which is a graph of the current as a function of time with indication of the standard deviation. The major difference according to the invention and the electrodes of the known art is immediately evident.

In a fully analogous experiment, three electrodes of the same type as used in the above comparative experiments, but with an electrolyte containing disodium hydrogen phosphate in a concentration of 0.3M, potassium dihydrogen phosphate in a concentration of 0.2M and potassium bromide in a concentration of 0.1M, were tested. The results appear from FIG. 3, (curve designated $10^{-1}$M Br$^-$), from which it is evident that these electrodes show an unacceptable drift.

I claim:
1. An electrode for polarographic measurement of the partial pressure of oxygen in gases or solutions, comprising a cathode in contact with and outwardly shielded by a gas permeable membrane, a silver/silver bromide half cell serving as anode and a bromide-containing aqueous electrolyte in contact with the cathode and the anode, the bromide ion concentration in the electrolyte being between $10^{-4}$ and $5 \times 10^{-3}$M.
2. An electrode as claimed in claim 1, wherein the bromide ion concentration is about $5 - 6 \times 10^{-4}$M.

* * * * *